United States Patent [19]

Samuels

[11] 4,405,563
[45] Sep. 20, 1983

[54] SCAVENGING NATURAL GAS STREAMS WITH SLURRY APPARATUS

[75] Inventor: Alvin Samuels, 444 Fairway Dr., New Orleans, La. 70124

[73] Assignees: Irwin Fox, Ballwin, Mo.; Alvin Samuels, New Orleans, La.; David Samuels, St. Louis, Mo.

[21] Appl. No.: 346,525

[22] Filed: Feb. 8, 1982

Related U.S. Application Data

[63] Continuation-in-part of Ser. No. 210,559, Nov. 26, 1980, abandoned.

[51] Int. Cl.³ .................................. B01D 50/00
[52] U.S. Cl. ........................... 422/169; 48/128; 55/91; 55/95; 55/234; 55/256; 55/267; 261/22; 261/95; 261/96; 261/123; 261/147; 261/149; 422/177
[58] Field of Search ............... 422/106, 112, 170, 171, 422/177, 169; 48/128; 261/22, 94–98, 123, 146, 147, 149, DIG. 9, DIG. 72; 55/21, 80, 87, 90, 91, 95, 213, 227, 234, 256, 267, 420

[56] References Cited

U.S. PATENT DOCUMENTS

| | | | |
|---|---|---|---|
| 2,151,248 | 3/1939 | Vaughan | 55/80 X |
| 2,715,521 | 8/1955 | Tatibana | 261/123 X |
| 2,849,294 | 8/1958 | Ruth | 422/106 |
| 2,867,425 | 1/1959 | Teller | 261/95 |
| 2,926,074 | 2/1960 | Berger | 422/106 |
| 3,011,969 | 12/1961 | Mader | 422/112 |
| 3,435,592 | 4/1969 | Lindenmaier et al. | 261/22 X |
| 3,907,510 | 9/1975 | Collins | 261/94 X |
| 4,039,289 | 8/1977 | Collins et al. | 261/94 X |
| 4,253,851 | 3/1981 | Brooks et al. | 55/90 |
| 4,312,646 | 1/1982 | Fattinger et al. | 261/22 X |

Primary Examiner—Richard L. Chiesa
Attorney, Agent, or Firm—Jerome A. Gross

[57] ABSTRACT

A system of apparatus is especially adapted to react gaseous contaminates of natural gas streams with a slurry of reactant particles and incorporates a contactor tower with a bottom gas inlet having a screen at its dynamic liquid level to confine downwardly a fill of packer-spacer material. Gas entering through the bottom inlet of the tower is divided by the packer-spacer material in tortuous flow paths maintained by the confining screen.

In advance of the contactor tower, after an inlet scrubber, is a heater which elevates the temperature of the gas before it enters the contactor tower. This avoids formation of clogging hydrates and liquefication of the gas. Using an outlet scrubber assures against entrance of droplets of any liquid into the pipeline.

6 Claims, 2 Drawing Figures

SCAVENGING NATURAL GAS STREAMS WITH SLURRY APPARATUS

CROSS REFERENCE TO RELATED APPLICATIONS

This application is a continuation-in-part of my pending application Ser. No. 210,559 filed Nov. 26, 1980, entitled "Slurry Apparatus for Sweetening Hydrocarbon Gas", now abandoned.

TECHNICAL FIELD

This invention relates to scavenging gaseous contaminants, particularly hydrogen sulfide, from natural gas streams by the use of slurry apparatus.

BACKGROUND ART

Gaseous contaminants of natural gas streams, particularly hydrogen sulfide, may be removed by the various processes reviewed in Maddox, Gas and Liquid Sweetening (1974) Campbell Petroleum Series. Most prominent among those, as a replacement for the classic iron oxide bed process, is the commercial amine process. Installations to carry out this process are expensive, and are not found feasible where gas wells are small and remote from each other.

Slurry processes for such a purpose have not found wide acceptance. In addition to the problem of reacting the hydrogen sulfide, other problems presented are excessive foaming, the danger of formation of hydrates which would clog the system, and incorporation of unacceptably large amounts of liquid and water into the gas stream.

DISCLOSURE OF THE INVENTION

A slurry contactor tower constructed as hereinafter set forth in combination with an inlet scrubber, a heater and an outlet scrubber, includes a screen at the dynamic liquid level which holds down a fill of packer spacers. The fill extends upward from the bottom gas inlet, and provides tortuous paths for slowly rising gas. The slurry of adsorbent particles is kept substantially in circulation along and across these paths by the rising gas itself; its slow rate of rise provides adequate time and opportunity for reaction with the adsorbent particles of the slurry while avoiding foaming.

Water and liquid hydrocarbon in the gas stream is eliminated in advance of the contactor vessel by a conventional scrubber at the inlet of the system. Then, formation of hydrates and hydrocarbon liquid in the contactor tower is avoided by the heater which, incorporated immediately prior to the tower, raises the gas temperature approximately 5.5° C. Gas so heated is introduced into the base of the contactor tower and expands the liquid slurry from the static level, to which it has originally been filled, to a substantial higher dynamic level as expanded by the upflow of gas. The gas passes slowly upward through the tortuous paths stabilized by the force of the screen on spacers, at a rate insufficient to cause serious foaming problems. The slow rise of gas which emerges in the headspace above the slurry permits droplets of liquid to fall out, without the use of a mist eliminator; but any remaining droplets of liquid water or liquid hydrocarbons are eliminated in an outlet scrubber, which is preferably similar to the inlet scrubber.

THE DRAWINGS

BEST MODE FOR CARRYING OUT THE INVENTION

Figure 1:
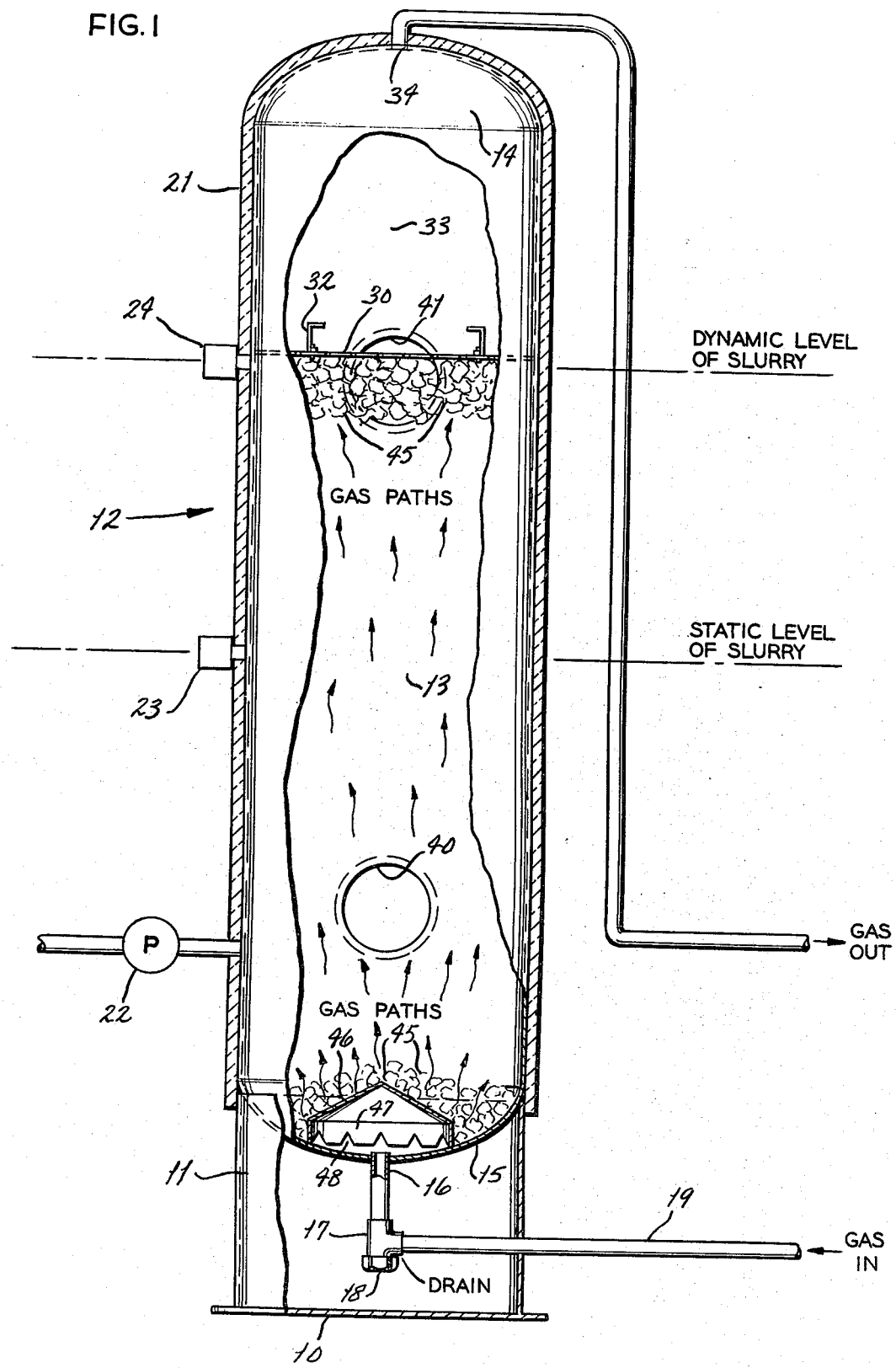
FIG. 1 is a side view principally in section of a contactor tower of the present invention.

FIG. 1 shows the unique contactor tower which, along with the other apparatus described, is utilized in the present invention to react gaseous contaminants.

Erected on a base plate 10 is a vertical hollow cylindrical support 11 of a contactor tower or reactor vessel generally designated 12. The tower 12 is of welded steel construction, having a heavy vertical cylindrical column portion 13, a domed top wall 14 and an inverted dome bottom wall 15 which slopes downward and inward to a central vertical gas inlet pipe 16. At the lower end of the gas inlet pipe 16 is a tee 17 whose lower end is closed by a removable drain cap 18. To the side opening of the tee 17 is connected a horizontal gas inlet pipe 19. The column portions 13 and top 14 are insulated with a conventional insulator jacket 21.

In the side of the vertical column portion 13 of the vessel 12 is a conventional pumped liquid inflow provision 22. Above this is a static liquid level sensor provision 23, located at a level designed to be the static level of the slurry, approximately at the mid-height of the vessel 12. At a still higher level, at which the liquid volume is about 50% greater, is an upper or dynamic liquid level sensor 24. At this level a confining screen 30 is provided, preferably in sections affixed by bolts to the lower side of channels 32 welded across the interior of the vessel 12. The confining screen 30 functions to hold down the packer spacers 45, hereinafter referred to, as the slurry expands as hereinafter discussed. The portion within the vessel 12 above the dynamic level of the slurry, that is, above the screen 30, is referred to as its headspace 33, which leads to a gas outlet 34 at the center of the domed top portion 14. Utilizing the design criteria herein discussed, it has been found best to leave the headspace 33 open, that is, without a conventional mist eliminator.

In the wall of the cylindrical columm portion 13 are located a lower access opening or manway generally designated 40 and an upper access opening or manway generally designated 41, both to be bolted sealedly in place as is conventional. The manways 40, 41 afford access to the interior including the screen 30 and permit fill of packing spacers 45, to be described, up to the level of and tightly against the screen.

Within the vessel 12 extending from its domed bottom 15 all the way to the confining screen is a continuous fill of packer spacers 45, which may be stainless steel or the familiar polypropylene rosettes, such as are sold under the commercial name PALL RINGS. The important characteristics of such spacers are that they be chemically inert under the conditions of operation and of such configuration that when packed on each other to provide an extensive series of surfaces spaced from each other, randomly arranged in a bed adequately pervious for bubbling gas through a particulate slurry. When the spacers are packed on each other, and held by the screen in contact with each other despite upflow of gas and its expansion of the slurry, they furnish a great multiplicity of flow paths for the gas entering from the central bottom inlet 16.

To obtain optimum distribution of the gas from the bottom inlet 16, it has a conical spreader cap 46 sloping at an angle of approximately 30° downward and outward to a short vertical cylindrical skirt 47 whose bottom edge, which rests on the vessel bottom wall 15, is there indented by a plurality of spreader openings 48.

It is to be understood that these described features are to be supplemented by features conventional in contactor towers, for example, further instrumentation and controls, provisions for sampling, and provisions for injecting chemicals such as thinning or viscosity-reducing agents.

Figure 2:
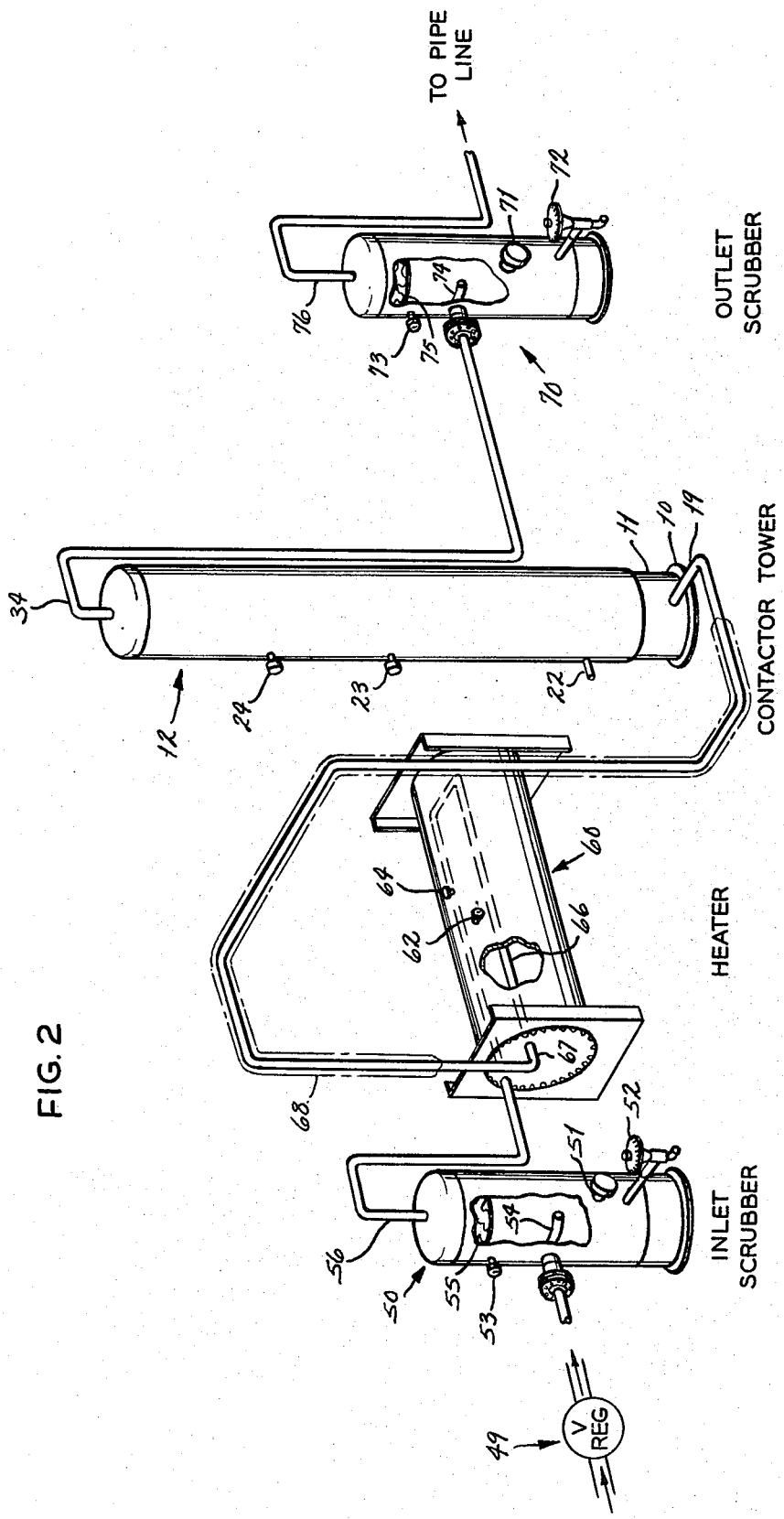
FIG. 2 is a schematic perspective view of the contactor tower of FIG. 1 in combination with an inlet scrubber and heater, which preceed it in the line of flow from a regulating valve to a pipeline, and an outlet scrubber which follows it in the flow line.

Referring now to FIG. 2, the contactor tower 12 is shown combined in an installation with an inlet scrubber generally designated 50, a heater generally designated 60 and an outlet scrubber generally designated 70. These are arranged in series in the line of flow from the regulator valve generally designated 49 which leads from a gas well, to a pipeline.

The inlet scrubber 50, heater 60 and outlet scrubber 70 are conventional. The inlet scrubber 50 has a conventional liquid level control 51 and a diaphragm operated liquid discharge valve 52. A pressure relief valve 53 is provided in the upper part of the scrubber vessel 70. Gas from a well, with its inflow volume regulated by the valve 49, enters the scrubber 50 through a tangential inlet diverter 54 and passes upward through a mist eliminator 55 to emerge from the top outlet 56 substantially free of water and liquid hydrocarbons.

The gas then enters the heater 60, which is preferably of the indirect heating water bath type, equipped with a temperature controller 62 and a pressure regulator 64. Its heating means is conventional and not shown; likewise not shown are its other conventional controls. The gas passes through the pipe coil 66 within the heater 60 and emerges through an outlet pipe 67, which is insulated by an insulating jacket 68 shown in phantom lines. The gas thus retains its heat as it flows to the inlet 19 of the contactor tower 12 for reacting gaseous contaminants without formation of hydrates or liquid hydrocarbon.

While this may be adequate to keep water and liquid hydrocarbon out of the pipeline, preferably the treated gas emerging from the outlet 33 is piped to the outlet scrubber 70, whose construction is similar to that of the inlet scrubber 50 and which functions to assure against any carry-over of liquid from the contactor tower 12 into the pipeline.

It includes a liquid level control 71, a liquid discharge valve 72 and a pressure relief valve 73. Gas enters it through a tangential inlet diverter 74, rises through a mist eliminator 75 and emerges through a top outlet 76, to be conducted thence to the pipeline.

Prior to use for sweetening sour natural gas, with the gas inlet 16 shut off by conventional valving not shown, the contactor tower 12 is first charged through its pumped inlet 22 up to the static liquid level sensor 23 with a water slurry of the chemical reactant to be used. The system described is useful for such reactant materials as the particulate iron oxide compound known commercially as SLURRISWEET, the particulate zinc compound known as CHEMSWEET, and familiar caustic washes. As an example, when the SLURRISWEET material is used, it may be mixed with water at roughly the rate of 100 lbs. per barrel.

The system of apparatus, including the contactor tower 12, as well as the inlet scrubber 50, heater 60 and outlet scrubber 70, are designed to accommodate with relatively little pressure drop the flow from a gas well to a pipe line as stabilized by a conventional flow regulator valve 49, which may be at the well head. The contactor tower is so proportioned as to accommodate the flow volume as between gas well pressure and pipe line pressure, permitting a rate of rise through the slurry sufficiently slow to avoid foaming, which has been found to be substantially 1.5 meters per second. The total pressure drop through the system, from the flow regulator valve 49 to the pipe line pressure, is preferably no greater than approximately 4–5 kg.

At an inflow rate and rate of rise so controlled and under the headspace pressure which so reflects the pipeline pressure, the slurry will expand upward to its designed dynamic level, that is, the level of the screen 30 at which the upper level sensor 24 is located. Despite the expansion of the slurry the packer spacers 45 are confined downwardly by the screen in contact with each other; they thus provide the multiplicity of tortuous paths referred to and stabilize the paths so that the flow of gas through them cannot join together or "channel" through the slurry.

While the dynamic liquid level has been referred to as at a volume about 50% greater than the static volume when no gas is bubbled through, the increase in volume may be lesser or greater—that is, in the range of about 30% to 70%. The rate of gas rise which avoids foaming will vary with the constituents of the gas stream, the reactive material utilized and additives conventionally used to effect foaming. In general, the size of the tower 12 will be varied directly as the gas flow rate and the absolute temperature, and inversely as to the operating pressure. Its height is minimized by the absence of a mist eliminator. With the slow rates of flow by which foaming is avoided, it has been found that headspace alone will suffice to permit coalescence of the mist-like particles of liquid which break from the surface at the dynamic liquid level; on their coalescence they drop back into the liquid. Use of the outlet scrubber 70 then provides all desired security against entrance of liquid into the pipeline.

With the slurry charged into the tower 12, the gas may be admitted through the system from the flow regulator valve 49 to flow inlet scrubber 50. As the gas flows through the tangential inlet diverter 54 and upward through the mist eliminator 55, entrained liquids, either water or liquid hydrocarbons, are separated from the gas stream and collected in the base of the scrubber, to be discharged through the motor valve 52. The operation of this valve and the level control 51 are conventional.

The gas exiting from scrubber 50 is then heated as it passes through the coil 66 of the heater 60. In the preferred embodiment, a fresh water bath solution is heated by a direct fired fire box to raise the temperature of the water bath to say about 65° to 85° C., or in general about 6° C. higher than its inlet temperature, under the control of the temperature controller 62. Preferably a thermostat (not shown) in the gas outlet 34 of the contactor tower 12 cooperates with the heater thermostat 64 to effect better control of the necessary heating operation. By it the gas temperature in the contactor vessel is prevented from dropping to the hydrate formation temperature and formation of hydrocarbon condensation is likewise prevented.

To the extent that liquid hydrocarbon or water may be present in the gas exiting from the tower at its outlet 34, they are separated out by the outlet scrubber 70, which functions in the same manner as the inlet scrubber 50 and in addition makes up for any lack of mist eliminator in the contactor tower 12. It is therefore useful in the event of a process upset which might otherwise permit slurry to be carried downstream.

Make-up water for the contactor tower solution may be introduced, using the pumped inlet 22. Thickening is remedied by conventionally injecting a thinning agent or viscosity-reducing agent into the vessel through a conventional chemical injection, not shown. If foaming occurs it can be substantially reduced or eliminated by similarly injecting a conventional defoaming agent.

Foaming can also be alleviated by reducing the superficial gas velocity of the sour gas entering the vessel. As a guide to the gas velocity which may be employed, this may be calculated from the empirical formula:

$$V_s = 2.09[Rho_e - Rho_g/Rho_g]^{0.325}$$

in which:

$V_s$ = maximum allowable superficial velocity feet per minute
$Rho_e$ = slurry density—pounds per cu. ft.
$Rho_g$ = gas density—pounds per cu. ft.

This guide is based on operation of the vessel at 100 pounds of particulate reactant material per barrel of water. With lesser amounts of reactant material the allowable superficial gas velocity may be increased, and with higher amounts it may be reduced, bearing in mind the desired rate of gas rise through the slurry.

While precise correlation between the actual dynamic liquid level of the slurry and the location of the confining screen 30 may not be maintainable continuously, it should be recognized that locating it too low will provide a liquid volume above it with lessened effectiveness for scavenging the hydrogen sulfide; while locating the screen too high will waste the headspace. Headspace is necessary to permit the mist-like particles of liquid, which break from the surface at the dynamic level, to precipitate and drop out of the gas. Apparently because of the low rate of gas rise through the liquid, the adequate headspace itself eliminates the need for demisting equipment, thus lowering the cost of the apparatus and of its maintenance.

It is understood that when the slurry of a reactant material has been substantially exhausted, the gas inflow must be cut off, drained through the removable cap 18 and disposed of, and the contactor vessel recharged with a fresh slurry before the gas stream is again directed through the system.

The various potential uses of the present apparatus, and modifications thereof to serve such uses, will from this disclosure be apparent to person skilled in the art.

INDUSTRIAL APPLICABILITY

The most significant industrial applicability of the present invention is believed to be in the provision of apparatus for sweetening sour natural gas from wells which are located at remote points or for other reasons do not justify the far greater expense of a commercial amine plant. However, because of relatively low initial costs and minimum maintenance requirements, its utilization in other applications may likewise prove to be of great value.

The embodiments of the invention in which an exclusive property or privilege is claimed are defined as follows:

1. For use in the line of flow from a natural gas well to a pipeline, a system of apparatus comprising in series, inlet scrubber means to separate out water and liquid hydrocarbons, means to raise the temperature of the gas so scrubbed sufficiently to avoid hydrate formation and hydrocarbon liquefaction in the contactor tower next defined, and a contactor tower including gas inlet means in its lower portion, top gas outlet means, a headspace below said top outlet means, and a downward-confining screen positioned at a design dynamic liquid level of a slurry of reactant particles to be filled in the tower, whereby packer-spacer material may be filled therein to extend upward from the level of the gas inlet means continuously to the screen and be held confined downward by the screen as such slurrly expands to the dynamic liquid level on passage of gas therethrough.

2. A system of apparatus as defined in claim 1, together with outlet scrubber means to separate out liquids interpositioned in the gas stream between the outlet means of the contactor tower and the pipeline.

3. A system of apparatus as defined in claim 1, in which said means to raise the temperature of the gas comprises means to raise its temperature substantially 6° C.

4. A system of apparatus as defined in claim 1, wherein the contactor tower is so proportioned that after having been filled with a reactant slurry together with such fill of packer-spacer material to and held down by the screen, and to such static liquid level, the slurry will expand and rise to such dynamic liquid level as the gas passes therethrough at a rate sufficiently slow to avoid foaming of the slurry.

5. A system of apparatus as defined in claim 1, said contactor tower being so proportioned that the volume from its bottom to the dynamic liquid level is substantially 1.5 times the volume to said static liquid level.

6. A system of apparatus as defined in claim 1, said contactor tower being so proportioned that the volume from its bottom to the dynamic liquid level is in the range of 1.3 to 1.7 times the volume to said static liquid level.

* * * * *

UNITED STATES PATENT AND TRADEMARK OFFICE
CERTIFICATE OF CORRECTION

PATENT NO. : 4,405,563

DATED : September 20, 1983

INVENTOR(S) : Alvin Samuels

It is certified that error appears in the above-identified patent and that said Letters Patent is hereby corrected as shown below:

Column 5, line 56, delete "person" and substitute ---persons---.

Column 6, line 29, delete "slurrly" and substitute ---slurry---.

Signed and Sealed this

Twenty-second Day of November 1983

[SEAL]

Attest:

GERALD J. MOSSINGHOFF

Attesting Officer

Commissioner of Patents and Trademarks